US009439445B2

(12) United States Patent
Perrier et al.

(10) Patent No.: US 9,439,445 B2
(45) Date of Patent: Sep. 13, 2016

(54) USE OF *L. CASEI* SSP. *PARACASEI* AS ANTIFUNGAL AGENT

(75) Inventors: Louise Perrier, Vigneux sur Seine (FR); Catherine Loysance-Paroux, La Meziere (FR); Yves Tirilly, Plougastel-Daoulas (FR); Benoit Fuhrmann, Les Essarts le Roi (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 12/746,125

(22) PCT Filed: Dec. 3, 2008

(86) PCT No.: PCT/FR2008/001679
§ 371 (c)(1),
(2), (4) Date: Sep. 21, 2010

(87) PCT Pub. No.: WO2009/098411
PCT Pub. Date: Aug. 13, 2009

(65) Prior Publication Data
US 2011/0045134 A1 Feb. 24, 2011

(30) Foreign Application Priority Data
Dec. 4, 2007 (FR) ..................................... 07 08451

(51) Int. Cl.
*A23C 9/123* (2006.01)
*C12R 1/245* (2006.01)

(52) U.S. Cl.
CPC ............. *A23C 9/1234* (2013.01); *C12R 1/245* (2013.01); *A23Y 2220/17* (2013.01)

(58) Field of Classification Search
CPC A23C 9/1234; C12R 1/245; A23Y 2220/17; A23Y 2220/63
See application file for complete search history.

(56) References Cited

U.S. PATENT DOCUMENTS

| 3,897,307 A * | 7/1975 | Porubcan | A23C 9/1232 426/61 |
| 5,378,458 A * | 1/1995 | Mayra-Makinen | A01N 63/00 424/93.3 |
| 6,399,055 B1 * | 6/2002 | Postaire et al. | 424/93.45 |
| 2003/0031756 A1 * | 2/2003 | Boufassa et al. | 426/46 |
| 2004/0038340 A1 * | 2/2004 | Deutscher et al. | 435/69.1 |
| 2005/0019894 A1 * | 1/2005 | Park | 435/252.9 |
| 2005/0095318 A1 * | 5/2005 | Schwenninger | A01N 63/00 426/61 |
| 2005/0255193 A1 * | 11/2005 | Kuma et al. | 426/43 |
| 2007/0098847 A1 * | 5/2007 | Teissier | 426/61 |
| 2007/0207187 A1 * | 9/2007 | Yajima et al. | 424/439 |
| 2010/0028492 A1 * | 2/2010 | Mogna | A23C 19/0973 426/43 |

FOREIGN PATENT DOCUMENTS

| EP | 0 302 300 | 2/1989 | |
| EP | 1 308 506 | 5/2003 | |
| EP | 1 683 425 | 7/2006 | |
| EP | 2153837 | * 2/2010 | ............. A61K 35/74 |
| FR | 2 775 420 | 9/1999 | |
| WO | WO 97/36603 | 10/1997 | |

OTHER PUBLICATIONS

Guerin-Danan et al. 1998. Milk fermented with yogurt cultures and Lactobacillus casei compared with yogurt and gelled milk: influence on intestinal microflora in healthy infants. Am J Clin Nutr. 67:111-117. Downloaded from: <URL: http://www.ajcn.org/content/67/1/111.full.pdf>.*
Sulieman Ameh and Tsenkova R. Sep. 2007. Manufacture and Quality of Fermented Milks Prepared Using Pure Strains of Lactic Acid Bacteria (LAB) and Yeast. Research Journal of Microbiology, 2(9): 684-689.*
Kim (KR 2003090581 Derwent abstract).*
Gourama, et al., "Inhibition of Growth and Mycotoxin Production of Penicillium by *Lactobacillus* Species", Lebensm.-Wiss. u.-Technol., 30, pp. 279-283, 1997.
Miescher, et al., "A Mixed Culture of *Propionibacterium jensenii* and *Lactobacillus paracasei* Subsp. *paracasei* . . . ", System. Appl. Microbiol., 27, pp. 229-237, 2004.
Tuma, et al., "Isolation of Antifungally Active Lactobacilli from Edam Cheese", Database FSTA accession No. 2008-00-p1429.

* cited by examiner

*Primary Examiner* — Felicia King
(74) *Attorney, Agent, or Firm* — Morgan, Lewis & Bockius LLP

(57) ABSTRACT

The invention relates to the use of *L. casei* ssp. *paracasei* for imparting antifungal properties to a fermented dairy product, and particularly for inhibiting the growth of molds of the Ascomycetes class in said product.

17 Claims, No Drawings

USE OF *L. CASEI* SSP. *PARACASEI* AS ANTIFUNGAL AGENT

RELATED APPLICATIONS

The present application is a U.S. National Phase Application of International Application No. PCT/FR2008/001679 (filed Dec. 3, 2008) which claims priority to French Patent Application No. 0708451 (filed Dec. 4, 2007) which are hereby incorporated by reference in their entirety.

The present invention relates to the use of *Lactobacillus casei* for protecting a milk product against the development of molds.

The use of microorganisms selected for the purpose of improving food storage has been known for thousands of years. Among these microorganisms, mention will be made of lactic acid bacteria, which are widely used for conserving milk products, meat products, or products of plant origin, intended for human food or animal feed. The improvement of food storage by means of lactic acid bacteria is to a large extent based on their ability to produce, during fermentation, lactic acid and other organic acids, which inhibit the growth of unwanted microorganisms (bacteria and molds) by reducing the pH of the medium, making it unfavorable to the growth of these microorganisms, and/or which have a direct toxic effect on said microorganisms. In addition to these organic acids, some lactic acid bacteria produce antifungal and/or antibacterial substances, such as hydrogen peroxide, diacetyl or nisin.

Application EP 0221499 describes antifungal properties of *Lactobacillus casei* ssp. *rhamnosus* NRRL-B-15972. When this bacterium is cultured on agar medium supplemented with cucumber juice, it is capable of completely inhibiting the growth of *Chaetomium olivacium*, and partially inhibiting the growth of *Aspergillus terreus* and of *Verticillium* sp. On the other hand, under these conditions, it has no effect on the growth of *Penicillium oxalicum*; an inhibitory effect on this microorganism is, however, observed with cultures of this bacterium on cucumber juice, at a pH of the order of 3.7.

Application EP 0576780 describes the antifungal effects of *Lactobacillus casei* ssp. *rhamnosus* LC-705. Cultures of this bacterium, obtained on a lactoserum-based medium, supplemented with casein hydrolysate and with yeast extract, can inhibit the growth of *Penicillium, Cladosporium, Fusarium* and *Candida*.

PCT application WO 97/36603 describes the antifungal effects of *Lactobacillus casei* ssp. *casei* N94/49432. Cultures of this bacterium, obtained on a synthetic medium supplemented with yeast extract, have an antifungal effect on *Alternaria, Chaetomtum, Cladosporium, Colletotrichum, Cunninghamella, Dothiorella, Geotrichum, Phoma* and *Phomopsis*.

Application EP 1308506 describes the antifungal and antibacterial effects of a combination of *Propionibacterium jensenii* with certain strains of *Lactobacillus casei* ssp. *paracasei*.

The inventors have now noted that bacteria of the species *Lactobacillus casei* ssp. *paracasei* have an antifungal activity, in particular on molds of the *Penicillium* genus, when they are used on their own, i.e. without being combined with other antifungal bacteria, and in particular with *Propionibacterium jensenii*.

This antifungal activity exhibits the following characteristics:

It does not develop when *L. casei* is cultured on synthetic medium, but appears when *L. casei* is cultured on milk, or a milk-based medium, starting from 5 hours of culture. It reaches its maximum after 24 to 48 h of fermentation.

It is sensitive to pH. It disappears below pH 4, but reappears, however, if the pH is brought back up above 4.

It is also sensitive to heat. It disappears after heat treatment for 1 minute at 60° C.

It is, moreover, not linked to the production of organic acids such as sorbic acid, propionic acid or benzoic acid (which are known for their antifungal activity), nor to that of hydrogen peroxide, these substances not being detectable in cultures of *L. casei* ssp. *paracasei* that have antifungal properties.

The subject of the present invention is the use of a bacterium of the species *L. casei* ssp. *paracasei*, for imparting antifungal properties to a fermented milk product.

In particular, the subject of the present invention is a method for inhibiting the development of a mold of the Ascomycete class, and in particular of the *Penicillium* genus, in a fermented milk product, characterized in that it comprises the fermentation of a milk substrate in the presence of a bacterium of the species *L. casei* ssp. *paracasei* for a period of time sufficient for the appearance of an antifungal activity in the substrate. This antifungal activity has the effect of inhibiting the development of said mold in the event of contamination of said product with said mold after the fermentation.

Advantageously, the amount of said bacterium of the species *L. casei* ssp. *paracasei* used to inoculate the milk substrate for said fermentation is at least $10^6$, preferably at least $10^7$, and advantageously between $10^7$ and $10^8$ cfu per gram of milk substrate.

According to one preferred embodiment of the method in accordance with the invention, the fermentation of said milk substrate is carried out for at least 5 hours, preferably for at least 15 hours, and entirely preferably for 24 to 48 hours. In order to obtain an antifungal activity using short fermentation times, it is preferable to use a relatively large amount of *L. casei* ssp. *paracasei*; for example, in order to observe an antifungal activity after 5 hours of fermentation of the milk substrate, the inoculation will be carried out in a proportion of at least $10^7$ cfu per gram of milk substrate.

According to another preferred embodiment of the method in accordance with the invention, it comprises, if necessary, adjustment of the pH of the fermented substrate to a value above 4, preferably between 4 and 6.5.

Advantageously, said bacterium of the species *L. casei* ssp. *paracasei* is a bacterium of the CNCM I-1518 strain. This strain is described in particular in application EP0794707; it was deposited, according to the provisions of the Treaty of Budapest, on Dec. 30, 1994, with the CNCM (Collection Nationale de Cultures de Microorganismes) [National Microorganism Culture Collection], 25 rue du Docteur Roux, in Paris.

The present invention will be understood more clearly from the further description which follows, which refers to examples illustrating the antifungal activity of a strain of *L. casei* ssp. *paracasei*.

EXAMPLE 1

Demonstration of the Antifungal Activity of Fermented Milk Products in the Presence of *L. Casei* Ssp. *Paracasei*

A fermented milk product containing *L. casei* ssp. *paracasei* (Actimel®, containing the CNCM I-1518 strain combined with *S. thermophilus* and *L. bulgaricus*), and a fermented milk product containing *S. thermophilus* and *L. bulgaricus* (control) were inoculated with 6 fungal species in a proportion of $10^2$ spores: *Mucor circinelloides* (2 strains tested); *Mucor plumbeus*; *Penicillium expansum*; *Penicillium roqueforti*; *Penicillium brevicompactum*.

These species are representative of the contaminations usually encountered on fresh milk products.

The products are then incubated at 10° C. and examined every 7 days for the appearance of fungal growth thalli.

Considerable development of the *Mucor* species is observed on the two products, from 14 days onward in the case of Actimel®, and from 7 days onward in the case of the control product. On the other hand, an extremely low growth (aggregates) or a lack of visible growth of *Penicillium* is observed on Actimel®, after 40 days of incubation, whereas an invasion of the surface of the control product is observed in only 14 days.

In a second series of experiments, the antifungal activity of the CNCM I-1518 strain was evaluated by means of a technique derived from the antibiogram technique. It consists in mixing the test product into agar (80% of product+ 20% of agar solution at 15 g/l) and in pouring the mixture into a Petri dish.

3 sterile paper disks are placed on the solidified medium, and 100 spores of the test mold (*P. expansum*. LMSA 00 083) are deposited onto the disks.

The Petri dishes are incubated at 25° C. and at 10° C. The diameter of the fungal thallus is measured regularly.

The products which were tested are the following: Actimel®; milk mix of Actimel® with *S. thermophilus* and *L. bulgaricus*, without the CNCM I-1518 strain; milk mix of Actimel® without *S. thermophilus* and *L. bulgaricus*, fermented for 24 hours in the presence of the CNCM I-1518 strain.

The results of two tests for each of the conditions tested are illustrated in Table I below.

The two products containing the CNCM I-1518 strain (Actimel®; and the milk mix of Actimel® fermented for 24 h with *L. casei* in the absence of *S. thermophilus* and *L. bulgaricus*) exhibit an antifungal activity, unlike the product which does not contain it (milk mix of Actimel® without *L. casei*).

EXAMPLE 2

Kinetics of Appearance of the Antifungal Activity During Fermentation by *L. Casei* Ssp. *Paracasei*

Antifungal activity tests were carried out on a mix made up of skimmed milk, supplemented with 2% of glucose and with 6% of milk proteins (conventional skimmed milk proteins), inoculated with $10^7$ cfu/ml of the CNCM I-1518 strain in freeze-dried form. Mix samples were taken before and after inoculation with CNCM I-1518, and then after 15 h, 24 h, 48 h and 72 h of fermentation. Prior to the antifungal activity tests, the samples taken and frozen were irradiated at 10 kG in order to block the development of the bacteria, so as to prevent their development and metabolism during the test. The test samples were thawed beforehand and the pH of the samples was adjusted to 6.2 (pH of the starting mix). The tests were carried out as described in Example 1 above.

The results of these tests (measurement of the diameter of the thallus) are shown in Table II below. The terms "thallus on disk" and "aggregates" refer to traces of fungal growth, observed only on the disk.

TABLE I

|  | Thallus diameter after incubation (mm) | | Thallus diameter (mm) after 17 days at 10° | | Thallus diameter after 24 days at 10° | |
| --- | --- | --- | --- | --- | --- | --- |
|  | Test 1 8 days at 25° C. | Test 2 7 days at 25° C. | Test 1 | Test 2 | Test 1 | Test 2 |
| Standard Actimel ® (commercially available) | 17.6 ± 4.4 | 19.2 ± 4.8 | 9.6 ± 0.5 | 10 ± 0.9 | 10.9 ± 0.8 | 12.9 ± 1.8 |
| Actimel ® without *L. casei* | >65 | >65 | >65 | >65 | >65 | >65 |
| Milk mix of Actimel ® fermented for 24 h with *L. casei* in the absence of *S. thermophilus* and *L. bulgaricus* | 9.4 ± 1 | 8.8 ± 1 | 11.4 ± 1 | 15.1 ± 1.2 | 14.1 ± 0.9 | 17.2 ± 1.2 |

TABLE II

| Noninoculated mix | Mix + *L. casei* | | | | |
|---|---|---|---|---|---|
| | To | T15 h | T24 h | T48 h | T72 h |
| | Test 7 days at 25° C. | | | | |
| 36.8 mm ± 10.2 | 22.5 mm ± 3.1 | 19.3 mm ± 2.7 | Aggregates | Aggregates | Aggregates |
| | Test 19 days at 10° C. | | | | |
| 48.5 mm ± 1.9 | 13.8 mm ± 3.3 | Thallus on disk | Aggregates | Aggregates | Aggregates |

These tests show the early appearance of the antifungal activity, which sometimes seems to be weakly present as early as the inoculation, but is clearly apparent only from 15 h of fermentation onward, and reaches a maximum between 24 h and 48 h. This activity is still present after 48 h and even 72 h provided that the pH is above 4.

EXAMPLE 3 pH Sensitivity of the Antifungal Activity

Antifungal activity tests were carried out under the same conditions as in Example 2 above, but without the pH being adjusted prior to the tests.

The results are shown in Table III below.

TABLE III

| | Noninoculated mix | Mix + *L. casei* | | | | |
|---|---|---|---|---|---|---|
| | | To | T15 h | T24 h | T48 h | T72 h |
| pH | 6.32 | 6.01 | 5.63 | 4.8 | 3.94 | 3.75 |
| | 33.2 ± 2.5 | 12.8 ± 1.3 | Aggregates | Aggregates | 34.3 ± 11.4 | 25.2 ± 2.1 |

These results show that the antifungal capacity is impaired when the pH is below 4.

This impairment appears, however, to be reversible, the antifungal capacity being restored if the pH is brought back to a value above 4.

EXAMPLE 4

Influence of the Fermentation Medium on the Antifungal Activity

In order to determine whether the antifungal activity was linked to the culture medium, tests were carried out using, as culture medium, firstly the milk mix described in Example 2, and secondly a synthetic medium, having the following composition: 10 g/L peptone; 10 g/l meat extract; 5 g/L yeast extract; 2 g/L dipotassium phosphate; 2 g/L ammonium citrate; 0.1 g/L magnesium sulfate; 0.05 g/L manganese sulfate; 20 g/L glucose; Tween 80:1 ml; qs 1 L deionized water. These media were inoculated with $10^7$ cfu/ml of the CNCM I-1518 strain in freeze-dried form. After 24 and 48 hours of culture, the antifungal activity was tested, as described in Example 2, for 7 days at 25° C. and 20 days at 10° C.

When the culturing is carried out on the milk mix, complete inhibition of the fungal growth is observed irrespective of the temperature of the test. On the other hand, no inhibition is observed when the culturing is carried out on the synthetic medium, for an equivalent bacterial population.

The invention claimed is:

1. A method of inhibiting development of a mold of the Ascomycete class in a fermented milk product, said method comprising
   fermentation of a milk substrate in the presence of a bacterium of the species *Lactobacillus casei* ssp. *paracasei* deposited with the Collection Nationale de Cultures de Microorganisms (CNCM) under Accession No. I-1518 without being combined with *Propionibacterium jensenii*, said fermentation being carried out for a period of time sufficient for the appearance of an antifungal activity in the substrate, said period of time being at least 15 hours, and said bacterium being cultured on milk or a milk based medium for at least 5 hours.

2. The method as claimed in claim 1, wherein the amount of said bacterium used to inoculate the milk substrate for said fermentation is at least $10^6$ cfu per gram of milk substrate.

3. The method as claimed in claim 2, wherein the amount of said bacterium used to inoculate the milk substrate for said fermentation is at least $10^7$ cfu per gram of milk substrate.

4. The method as claimed in claim 1, comprising adjustment of the pH of the fermented substrate to a value above 4.

5. The method as claimed in claim 1, wherein said mold of the Ascomycete class belongs to the *Penicillium* genus.

6. The method as claimed in claim 1, wherein the said period of time is between 24 hours and 48 hours.

7. The method as claimed in claim 1, comprising adjustment of the pH of the fermented substrate to a value between 4 and 6.5.

8. The method as claimed in claim 1, wherein the fermentation of the milk substrate is performed in the absence of *Streptococcus thermophilus* and *Lactobacillus bulgaricus*.

9. The method as claimed in claim 1, wherein the method excludes culturing the bacterium on a synthetic medium without the milk or milk based medium.

10. A method of inhibiting the development of a mold of the Ascomycete class in a fermented milk product, said method comprising
    culturing a bacterium of the species *Lactobacillus casei* ssp. *paracasei* deposited with the Collection Nationale de Cultures de Microorganisms (CNCM) under Accession No. I-1518 without being combined with *Propionibacterium jensenii* on milk or a milk based medium for at least 5 hours, and fermenting a milk substrate in the presence of the cultured bacterium for at least 15 hours.

11. The method as claimed in claim 10, wherein the amount of said bacterium used to inoculate the milk substrate for said fermenting is at least $10^6$ cfu per gram of milk substrate.

12. The method as claimed in claim 11, wherein the amount of said bacterium used to inoculate the milk substrate for said fermenting is at least $10^7$ cfu per gram of milk substrate.

13. The method as claimed in claim 10, comprising adjusting pH of the fermented milk substrate to a value above 4.

14. The method as claimed in claim 10, wherein said mold of the Ascomycete class belongs to the *Penicillium* genus.

15. The method as claimed in claim 10, wherein the said period of time is between 24 hours and 48 hours.

16. The method as claimed in claim 10, comprising adjusting pH of the fermented milk substrate to a value between 4 and 6.5.

17. The method as claimed in claim 10, wherein the fermenting is performed in the absence of *Streptococcus thermophilus* and *Lactobacillus bulgaricus*.

* * * * *